United States Patent [19]

Hammen et al.

[11] 3,950,350

[45] Apr. 13, 1976

[54] PENAM-DIMETHYLSULFOXIDE COMPLEX

[75] Inventors: Philip D. Hammen, East Lyme; Stephen S. Massett, Groton, both of Conn.

[73] Assignee: Pfizer Inc., New York, N.Y.

[22] Filed: Dec. 27, 1974

[21] Appl. No.: 536,718

[52] U.S. Cl.... 260/306.7 C; 260/294.8 C; 424/263; 424/270
[51] Int. Cl.² ........................................ C07D 277/04
[58] Field of Search ............... 260/306.7 C, 306.7 R

*Primary Examiner*—R. Gallagher
*Assistant Examiner*—D. B. Springer
*Attorney, Agent, or Firm*—Connolly and Hutz

[57] ABSTRACT

6-(Triphenylmethylamino)-2,2-dimethyl-3-(N-[p-methoxybenzyl]carbamoyl)penam-dimethylsulfoxide complex as a useful intermediate leading to the synthesis of antibacterial 6-acylamino-2,2-dimethyl-3-(5-tetrazolyl)penams.

1 Claim, No Drawings

PENAM-DIMETHYLSULFOXIDE COMPLEX

BACKGROUND OF THE INVENTION

This invention relates to an intermediate which is useful in the preparation of novel antibacterial agents which are of value as animal feed supplements, as therapeutic agents for the control of infectious diseases caused by gram-positive and gram-negative bacteria, and for the sterilization of hospital surfaces and the like.

SUMMARY OF THE INVENTION

It has now been found that the solid complex of 6-(triphenylmethylamino)-2,2-dimethyl-3-(N-[p-methoxybenzyl]carbamoyl)penam and dimethylsulfoxide is a useful intermediate leading to the synthesis of 6-acylamino-2,2-dimethyl-3-(5-tetrazolyl)penams, a useful class of antibacterial agents.

DETAILED DESCRIPTION OF THE INVENTION

The 6-(triphenylmethylamino)-2,2-dimethyl-3-(N-[p-methoxybenzyl]carbamoyl)penam of the complex of the present invention is conveniently synthesized from the known 6-(triphenylmethylamino)-2,2-dimethyl-3-carboxypenam by a reaction illustrated as follows:

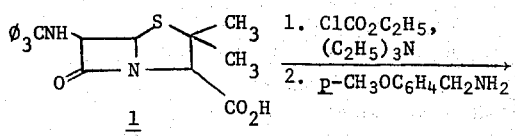

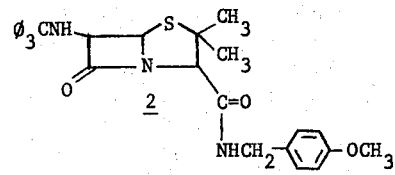

In practice, compound 1 is contacted with at least an equimolar amount of triethylamine and ethyl chloroformate in a reaction-inert solvent such as chloroform at ice-bath temperature for a period of 30–45 minutes. The mixed anhydride, generated in situ, is then reacted with at least an equimolar amount of p-methoxybenzyl amine, giving 2.

Compound 2 can be isolated by conventional means by concentration of the chloroform and treatment of the concentrate with water, followed by separation of the chloroform layer and its subsequent concentration to dryness. Compound 2, obtained by this process, is amorphous in nature and contains impurities which partially or completely preclude its reaction in subsequent synthetic steps leading to the desired antibacterial agents.

It has been discovered that if the above-mentioned chloroform solution, prior to concentration to dryness, is treated with dimethylsulfoxide, concentrated further and cooled, there results a precipitate of the desired intermediate amide as a 1:1 complex with dimethylsulfoxide. The solid complex can be filtered, washed with dimethylsulfoxide and stored for further use or the free amide generated from it.

Alternately, the crude and impure amide, isolated without benefit of dimethylsulfoxide, can be dissolved in an appropriate solvent such as methylene chloride, benzene, ethyl acetate, chloroform or tetrahydrofuran and treated with dimethylsulfoxide. The solvent is subsequently concentrated in vacuo and the resulting solution cooled in an ice-bath. Th resulting precipitated complex is filtered, washed with dimethylsulfoxide and dried. As one skilled in the art might anticipate, the crude amide can also be added directly to dimethylsulfoxide without benefit of solvent, and the resulting solid complex filtered and treated as previously mentioned.

Regarding the amount of dimethylsulfoxide to be used in forming the complex of the present invention, 0.5–10 ml. of dimethylsulfoxide per gram of amide is operable, with a preferred range of 1–2 ml. per gram. In addition, when dimethylsulfoxide is used as a solvent, it is preferred that it be concentrated in vacuo prior to cooling and filtration of the complex.

As previously mentioned, the complex of the present invention can be treated in a manner to generate the free amide from said complex. This is achieved by partitioning the complex between water and a water-immiscible solvent such as chloroform. In practice, the complex is added to chloroform or a suitably described solvent and extracted several times with water. The organic layer is separated, dried and concentrated to provide the pure amide.

The free amide is, as previously discussed, useful in the synthesis of antibacterial agents. A flow diagram showing the conversion of said amide to the antibacterial penams is depicted as follows:

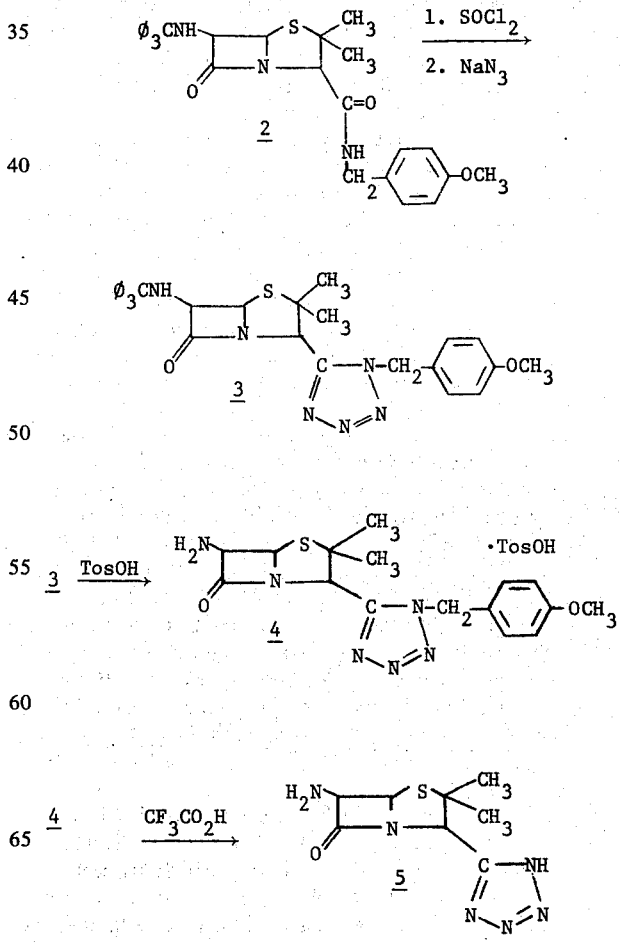

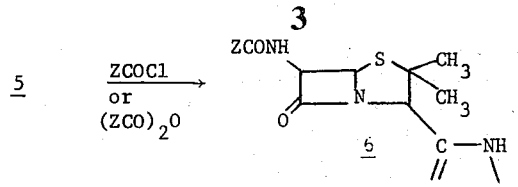

wherein ZCOCl and (ZCO)₂0 are acylating agents.

In the first step of this conversion, compound 2 is converted to the tetrazole, 3, through formation of the imino chloride with thionyl chloride followed by reaction of said imino chloride with sodium azide in a reaction-inert solvent such as methylene chloride. In practice, the amide, 2, in a solvent cooled to ice bath temperature is treated with at least an equivalent amount of thionyl chloride and an excess of an acid-binding agent such as pyridine. After stirring at ambient temperature for 1–2 hours, one to two equivalents of sodium azide in chloroform, containing some methanol, is added and the stirring continued for an hour. The resulting mixture is quenched in water and the product isolated from the dried organic solvent layer.

In the next step of this conversion, the 6-amino group of 3 is deblocked by removal of the triphenylmethyl moiety with p-toluenesulfonic acid hydrate. It is preferred that said reaction be conducted in a reaction-inert solvent which will facilitate precipitation of the resulting tosylate acid addition salt and also solubilize the starting reagents. Such solvents as ethers, dialkyl ketones or chlorinated hydrocarbons are suitable, with the preferred solvent being acetone.

More specifically, one mole of p-toluenesulfonic acid hydrate is contacted with an equimolar amount of the penam derivative in the appropriate solvent for from 1 to 60 minutes at ambient temperatures. The resulting tosylate salt of the product is filtered. The crude product can be used as isolated or may be triturated in a suitable solvent. The free amino compound can be isolated from the salt in the usual manner, but since p-toluenesulfonic acid is used in the next step of the sequence, it is advantageous to utilize the acid addition salt as isolated.

The next step in the synthetic route (4 → 5) leading to final antibacterial products, is removal of the penam tetrazole protecting group, p-CH-hd OC₆H₄CH₂ $_{p\text{-}CH3}$ In practice, the tosylate acid addition salt in anisole is treated with an excess of trifluoroacetic acid at 40°±5° C. for from 5–45 minutes. The trifluoroacetic acid acts as reagent and solvent in the solvolysis reaction.

Following completion of the reaction, the excess trifluoroacetic acid and anisole are removed under reduced pressure and the residual trifluoroacetic acid addition salt treated with base and acid under extracting conditions familiar to those skilled in the art, to generate the free 6-amino-2,2-dimethyl-3-(tetrazolyl)penam, 5.

Acylation of compound 5 is carried out by a procedure familiar to one skilled in the art. The acylating species, either an acid halide or anhydride, is added to 6-amino-2,2-dimethyl-3-(tetrazolyl)penam in a solution of chloroform containing at least two equivalents of a tertiary amine such as triethylamine or pyridine. The reaction time is approximately 10–60 min. at ambient temperatures. The product is isolated by quenching the reaction mixture in water, followed by removal of basic material through an acid wash and subsequent extraction of the product from the chloroform with aqueous base. Acidification of the aqueous solution liberates the product, which can be filtered or extracted with a water immiscible solvent.

The antibacterial penam compounds, 6, show activity against a wide variety of gram-positive and gram-negative bacteria. The in vitro activity can be demonstrated by the conventional two-fold serial dilution technique in Brain-Heart Infusion broth (Difco). The broth is inoculated with the bacterial culture, and with the test antibiotic, and then it is incubated overnight. On the next day, the test is read visually. The minimum inhibitory concentration (MIC) is the lowest concentration of antibiotic which prevents turbidity, i.e., which prevents growth of the microorganism. In vitro activities of several of the penam compounds of the invention are presented later in this specification.

The in vitro activity of the antibacterial compounds, 6, makes them particularly suitable for topical application, for example, in the form of creams and ointments, and for the sterilization of sick-room and hospital surfaces, equipment, and the like.

These antibacterial penam compounds are also active in vivo. In determining such activity, the test antibiotic is administered to infected mice, using a multiple dosing regimen. The severity of the infection varies from about one to about ten times the dose needed to kill 100% of the mice under the conditions of the test. At the end of the test, the activity of a compound is assessed by counting the number of survivors among the treated animals. Both the subcutaneous (SC) and oral (PO) dosage routes are used. Results are given in Table I for two compounds produced from the novel intermediate of the invention. The ability of the compounds to protect mice against systemic infections caused by a lethal intraperitoneal inoculum of *Staphylococcus aureus* or of *Escherichia coli* is presented.

TABLE I.

| Compound | Dosage (mg./kg.) | Dosage | Percentage Protection S. aureus | E. coli |
|---|---|---|---|---|
| 6-(D-2-amino-2-[3-thienyl]acetamido)-2,2-dimethyl-3-(5-tetrazolyl)penam | 50 | SC | 40 | 20 |
| " | 25 | SC | 60 | 20 |
| " | 12 | SC | 50 | |
| " | 6 | SC | 50 | |
| " | 200 | PO | | 0 |
| 6-(D-2-amino-2-[p-hydroxyphenyl]acetamido)-2,2-dimethyl-3-(5-tetrazolyl)penam | 50 | SC | 80 | 100 |
| " | 25 | SC | 70 | 80 |
| " | 12 | SC | 50 | |
| " | 6 | SC | 50 | |
| " | 200 | PO | | 100 |

The in vivo activity of these antibacterial compounds makes them suitable for the control of bacterial infections in mammals, including man, by both the oral and parenteral modes of administration. The compounds will find wide use in the control of infections caused by susceptible gram-positive and gram-negative bacteria in human subjects.

The daily dosages of the penams, 6, to be used in human subjects will not differ significantly from other, clinically-used, penam antibiotics. The prescribing physician will ultimately determine the appropriate dose for a given human subject, and this can be expected to vary according to the age, weight and response of the individual patient, as well as the nature and the severity of the patient's symptoms. These compounds will normally be used orally at dosages in the range from about 10 to about 200 mg. per kilogram of body weight per day, and parenterally as dosages from about 5 to about 100 mg. per kilogram of body weight per day. These figures are illustrative only, however, and in some cases it may be necessary to use dosages outside these limits.

The following examples are provided solely for the purpose of further illustration. Infrared (IR) spectra are measured as potassium bromide discs (KBr discs) or as Nujol mulls, and diagnostic absorption bands are reported in wave numbers ($cm^{-1}$). Nuclear magnetic resonance spectra (NMR) are measured at 60 MHz for solutions in deuterochloroform ($CDCl_3$), perdeutero dimethyl sulfoxide (DMSO-$d_6$) or deuterium oxide ($D_2O$), and peak positions are expressed in parts per million (ppm) downfield from tetramethylsilane or sodium 2,2-dimethyl-2-silapentane-5-sulfonate. The following abbreviations for peak shapes are used: s - singlet; d - doublet; t - triplet; q - quartet; m - multiplet.

EXAMPLE 1

6-(Triphenylmethylamino-2,2-dimethyl-3-(N-[p-methoxybenzyl]carbamoyl)penam

A. Without the Dimethylsulfoxide Complex

To a stirred slurry of 216 g. of 6-aminopenicillanic acid in 1,500 ml. of anhydrous chloroform is added 278 ml. of triethylamine, and the mixture stirred at ambient temperature until a clear solution is obtained. The solution is cooled to about 0° C., and 306 g. of triphenylmethyl chloride is added. Stirring is continued at about 0° C., for 30 min., and at ambient temperature for a further 24 hrs. The mixture is cooled to about 0° C., and 14 ml. of triethylamine, followed by 95 ml. of ethyl chloroformate, is added. During this process the temperature rises to about 15° C., and a precipitate forms. To facilitate stirring a further 200 ml. of chloroform is added. The stirring is continued for 30 min. Then at about 0° C., 50 ml. of p-methoxybenzylamine is injected into the reaction medium, below the surface of the solvent. At 10 minute intervals, three further aliquots of p-methoxybenzylamine (35 ml., 25 ml. and 21 ml.) are injected in the reaction in similar fashion. The total volume of p-methoxybenzylamine added is 126 ml. The cooling bath is then removed, and the reaction is stirred for a further 1 hour. The chloroform solution is washed successively with five 2,000-ml. portions of water and one 2,000-ml. portion of saturated brine. The chloroform is finally dried using anhydrous sodium sulfate. The reaction is concentrated in vacuo giving crude 6-(triphenylmethylamino)-2,2-dimethyl-3-(N-[p-methoxybenzyl]carbamoyl)penan, as an amorphous solid.

B. Using Dimethysulfoxide Complex

To a solution of 45.9 g. (0.1 mole) of 6-triphenylmethylaminopenicillanic acid, triethylamine salt, prepared according to Example 1-A, in approximately 200 ml. of chloroform cooled to 5° C. is added dropwise 9.5 ml. (0.1 mole) of ethyl chloroformate, and the resulting solution allowed to stir for 15 min. Four equal portions comprising a total of 13.1 ml. (0.1 mole) of p-methoxybenzylamine are added successively beneath the surface of the reaction mixture. Following completion of the addition, the reaction is allowed to stir 30 min. at 10°–15° C. and 30 min. at room temperature. Subsequently, 150 ml. of water is added to quench the reaction, and the chloroform layer separated, washed with 4 × 50 ml. of water and dried over magnesium sulfate. Dimethylsulfoxide (120 ml.) is added to the dried organic layer and the solution concentrated to approximately 200 ml. and cooled to 20° C. The resulting precipitate of 6-(triphenylmethylamino)-2,2-dimethyl-3-(N-[p-methoxybenzyl]carbamoyl)penamdimethylsulfoxide complex is filtered, washed with water and dried, DTA (differential thermal analysis) - 153° C.

Anal. Calc'd for $C_{35}H_{35}N_3O_3S.C_2H_6SO$: C, 66.8; H, 6.3; N, 6.4; S, 9.8. Found: C, 68.2; H, 6.2; N, 6.3; S, 9.6.

The above complex is added to 200 ml. of water. The chloroform layer is separated, dried and concentrated to dryness to provide crystalline 6-(triphenylmethylamino)-2,2-dimethyl-3-(N-[p-methoxybenzyl]carbamoyl)penam, 33.8 g. (58% yield), DTA = 162° C.

EXAMPLE 2

6-(Triphenylmethylamino)-2,2-dimethyl-3-(1-[p-methoxybenzyl]tetrazol-5-yl)penam

To 2.3 ml. of methylene chloride is added 5.77 g. (10 m moles) of 6-(triphenylmethylamino)-2,2-dimethyl-3-(N-[p-methoxybenzyl]carbamoyl)penam purified through the dimethylsulfoxide complex of Example 1-B, followed by 3.95 ml. of pyridine, and the resulting solution cooled to 0° C. To this solution is added dropwise 0.9 ml. of thionyl chloride, and the reaction mixture allowed to stir at ambient temperature for 90 min. Sodium azide (1.1 g., 17 m moles) in 13.7 ml. of chloroform containing 150 mg. of phosphorous oxychloride and 90 mg. of methanol is added to the reaction mixture and the stirring at room temperature continued for one hour. The reaction is subsequently quenched in 200 ml. of water and 100 ml. of chloroform and the layers separated. The organic layer is dried over sodium sulfate and concentrated under reduced pressure to 25 ml. Isopropanol (100 ml.) is added and the remainder of the chloroform and isopropanol is removed in vacuo. The residue is allowed to granulate overnight to provide the desired intermediate as a crystalline solid, 3.4 g. (57% yield). Further purification can be effected by recrystallization from water, m.p. 178°–182° C. The infrared spectrum (KBr disc) of the products shows an absorption band at 1790 $cm^{-1}$ ($\beta$-lactam carbonyl). The NMR spectrum (in $CDCl_3$) shows absorption bands at 7.25 ppm (multiplet, aromatic hydrogens), 5.50 ppm (broad singlet, benzyl hydrogens), 5.05 ppm (singlet, C-3 hydrogen), 4.40 ppm (broad singlet, C-5 and C-6 hydrogens), 3.80 ppm (singlet, methoxy hydrogens), 1.45 ppm (singlet, C-2 methyl hydrogens) and 0.70 ppm (singlet, C-2 methyl hydrogens).

When this reaction is repeated using the amorphous product of Example 1-A, only a gum is isolated.

EXAMPLE 3

6-Amino-2,2-dimethyl-3-(5-tetrazolyl)penam

A.

6-Amino-2,2-dimethyl-3-(1-[p-methoxybenzyl]tetrazol-5-yl)penam p-toluenesulfonate To a stirred slurry of 143 g. of 6-(triphenylmethylamino)-2,2-dimethyl-3-(1-[p-methoxybenzyl]tetrazol-5-yl)penam in 1,000 ml. of dry acetone at room temperature is added 45.0 g. of p-toluenesulfonic acid monohydrate, resulting in a clear solution. After about 15 min. the product starts to precipitate. Stirring is continued for a further 45 min. after the product starts to appear, and then a first crop of product is filtered off and washed with chloroform. The acetone is evaporated to dryness, and the solid residue is slurried for 45 min. in 300 ml. of chloroform. This affords a second crop of product. The two crops are combined, slurried for 1 hr. in 1,000 ml. of chloroform, filtered, and dried in vacuo, providing 123 g. of 6-amino-2,2-dimethyl-3-(1-[p-methoxybenzyl]tetrazol-5-yl)penam p-toluenesulfonate, m.p. 174°–175.5° C. The infrared spectrum (KBr disc) of the product shows an absorption band at 1795 $cm^{-1}$. The NMR spectrum (in DMSO-$d_6$) shows absorption bands at 7.20 ppm (multiplet, aromatic hydrogens), 5.80 ppm (multiplet, benzyl hydrogens, C-5 hydrogen and C-3 hydrogens), 5.20 ppm (doublet, C-6 hydrogen), 3.75 ppm (singlet, methoxy hydrogens), 2.35 ppm (singlet, sulfonate methyl hydrogens), 1.70 ppm (singlet, C-2 methyl hydrogens) and 0.85 ppm (singlet, C-2 methyl hydrogens).

B.

6-Amino-2,2-dimethyl-3-(1-[p-benzyloxybenzyl]tetrazol-5-yl)penam

A solution consisting of 558 mg. of 6-(triphenylmethylamino)-2,2-dimethyl-3-(1-[p-benzyloxybenzyl]tetrazol-5-yl)penam, 156 mg. of p-toluenesulfonic acid monohydrate and 1 ml. of acetone is stored at ambient temperature for 2.5 hrs. It is then added with stirring to 50 ml. of ether. After stirring for a further 10 min., the solid which precipitates is filtered. This affords 394 mg. of the p-toluenesulfonate of the product. A 304-mg. aliquot of this p-toluenesulfonate salt is dissolved in 10 ml. of methylene chloride, and to the solution is added 69.7 μl. of triethylamine. After 3 min., 5 ml. of water is added and the mixture is stirred vigorously. The organic phase is then separated off, diluted with ether, dried over anhydrous magnesium sulfate, and evaporated to dryness in vacuo. The residue is 189 mg. (69% yield) of 6-amino-2,2-dimethyl-3-(1-[p-benzyloxybenzyl]tetrazol-5-yl)penam. The NMR spectrum (in $CDCl_3$) of the product shows absorption bands at 7.40 ppm (singlet, phenyl hydrogens), 7.15 ppm (quartet, phenylene hydrogens), 5.55 ppm (broad singlet, C-5 and benzyl hydrogens), 5.20 ppm (singlet, C-3 hydrogens), 5.10 ppm (singlet, benzyl hydrogens) 4.60 ppm (doublet, C-6 hydrogen), 1.50 ppm (singlet, C-2 methyl hydrogens) and 0.90 ppm (singlet, C-2 hydrogens).

C. 6-Amino-2,2-dimethyl-3-(5-tetrazolyl)penam

A stirred solution of 32.0 g. of 6-amino-2,2-dimethyl-3-(1-[p-methoxybenzyl]tetrazol-5-yl)penam p-toluenesulfonate, and 24 ml. of anisole, in 96 ml. of trifluoroacetic acid is maintained at 40° ± 1° C. for 35 min. The trifluoroacetic acid is then removed rapidly by vacuum distillation. A 120-ml. portion of ether is added to the residue, which produces a white flocculent suspension. The suspension and solvent is cooled to about 0° C., and to it is then added, portionwise, 80 ml. of 2N sodium hydroxide, giving two clear phases. The pH of the aqueous phase at this point is about 2.7. The layers are separated, and the ether phase is discarded. The pH of the aqueous phase is raised to 4.1 with 2N sodium hydroxide. This aqueous phase is then washed with 100 ml. of ether and filtered. It is combined with the corresponding aqueous phases from four other identical experiments, and the total aqueous solution is lyophilized to give crude 6-amino-2,2-dimethyl-3-(5-tetrazolyl)penam. This crude product is slurried in a small amount of water and filtered off. It is then re-suspended in water and brought into solution by raising the pH to 7.4 by the addition of sodium hydroxide solution. The clear solution is extracted with ether and the extracts are discarded. The pH of the aqueous phase is adjusted to 4.1 using dilute hydrochloric acid, and the product which precipitates is filtered off. The infrared spectrum of the product shows an absorption at 1795 $cm^{-1}$. Its NMR spectrum (in DMSO-$d_6$) shows absorptions at 5.65 ppm (doublet C-5 hydrogen), 5.20 ppm (singlet, C-3 hydrogen), 4.70 ppm (doublet, C-6 hydrogen), 1.65 ppm (singlet, C-2 methyl hydrogens) and 1.10 ppm (singlet, C-2 methyl hydrogens).

EXAMPLE 4

Acylation of 6-Amino-2,2-dimethyl-3-(5-tetrazolyl)penam 6-(2-Phenylacetamido)-2,2-dimethyl-3-(5-tetrazolyl)penam A flask containing 965 mg. of 6-amino-2,2-dimethyl-3-(1-[p-methoxybenzyl]tetrazol-5-yl)penam p-toluenesulfonate, 40 drops of anisole, and 5 ml. of trifluoroacetic acid is immersed in a water-bath maintained at 35°–40° C. The progress of the reaction is followed by removing samples at intervals, and recording their nuclear magnetic resonance spectra. After about 25 min., the removal of the p-methoxybenzyl group is found to be approximately 90% complete. At this point the reaction solution is added to a rapidly-stirred, ice-cold solution of 10 ml. of pyridine in 50 ml. of chloroform. The stirring is continued for 5 min., and then 0.24 ml. of phenylacetyl chloride is added. The cooling bath is removed and the reaction mixture is stirred for a further 20 min. A 100-ml. portion of water is added, and the pH of the aqueous phase is then adjusted to 2.5 by the dropwise addition of 0.5N hydrochloric acid. The chloroform layer is separated off, washed with saturated brine, dried using anhydrous sodium sulfate and then evaporated to dryness in vacuo. The crude product thus obtained is re-dissolved in chloroform, and the solution is divided into two equal portions. To one of these portions is added an equal volume of water. The layers are stirred vigorously and the pH of the aqueous phase is raised to 6.9 by the dropwise addition of 0.1N sodium hydroxide solution. The chloroform is separated off and discarded, and then an equal quantity of fresh chloroform is added to the aqueous phase. The layers are stirred vigorously and the pH is adjusted to 2.5 using dilute hydrochloric acid. The chloroform is separated off, washed with saturated brine, dried using anhydrous magnesium sulfate and then evaporated to dryness in vacuo. This affords 197 mg. of an oily residue. The residue is re-dissolved in 3 ml. of chloroform which is then added dropwise to 30 ml. of hexane. The fluffy white solid which precipitates is filtered off, giving 80 mg. of 6-(2-phenylacetamido)-2,2-dimethyl-3-(5-tetrazolyl)penam. The infrared spectrum (KBr disc) of the product shows absorption bands at 1795 cm$^{-1}$ ($\beta$-lactam carbonyl), 1660 cm$^{-1}$ (amide I band) and 1510 cm$^{-1}$ (amide II band). The NMR spectrum (in CDCl$_3$) shows absorption bands at 7.20 ppm (broad singlet, aromatic hydrogens), 5.55 ppm (multiplet, C-5 and C-6 hydrogens), 5.15 ppm (singlet, C-3 hydrogens), 3.60 ppm (broad singlet, benzyl hydrogens), 1.40 ppm (singlet, C-2 methyl hydrogens) and 1.05 ppm (singlet, C-2 methyl hydrogens).

EXAMPLE 5

In vitro antibacterial activities for a number of compounds prepared by the procedure of Example 4 are presented below.

In Table II, the minimum inhibitory concentrations (MIC's) of numerous compounds against a strain of Streptococcus pyogenes, are reported.

TABLE II

| Z CO— | MIC ($\mu$g/ml) vs. Strep. pyogenes |
|---|---|
| 2-phenylacetyl | <0.1 |
| 3-(o-chlorophenyl)-5-methyl-4-isoxazole-carbonyl | <0.1 |
| 2-azido-2-phenylacetyl | <0.1 |
| 2-cyanoacetyl | 0.1 |
| 2-(1-tetrazolyl)acetyl | <0.39 |
| 2-phenoxyacetyl | <0.1 |
| phenoxycarbonyl | <0.1 |
| benzyloxycarbonyl | <0.1 |
| ethoxycarbonyl | <0.1 |
| acetyl | <0.1 |
| 2-bromoacetyl | <0.1 |

TABLE II-continued

| Z CO— | MIC ($\mu$g/ml) vs. Strep. pyogenes |
|---|---|
| 2-(4-pyridylthio)acetyl | <0.1 |
| 2-(N,N'-diethylamidinothio)acetyl | <0.1 |
| hydrogen | <0.1 |
| 3-(carbamoyl)acryloyl | <0.1 |
| 2,6-dimethoxybenzoyl | <0.2 |
| D-2-amino-2-phenylacetyl | <0.1 |
| D-2-amino-2-(m-hydroxyphenyl)acetyl | <0.1 |
| DL-2-amino-2-(3,4-dihydroxyphenyl)acetyl | <0.1 |
| L-2-amino-2-(p-hydroxyphenyl)acetyl | <0.1 |
| D-2-amino-2-(2-thienyl)acetyl | 0.1 |
| DL-2-amino-2-(p-]N,N-dimethylamino]-phenyl)acetyl | 0.39 |
| D-2-amino-2-(3-chloro-4-hydroxyphenyl)-acetyl | 0.1 |
| DL-2-amino-2-(p-chlorophenyl)acetyl | <0.1 |
| DL-2-amino-2-(m-chlorophenyl)acetyl | 0.78 |
| DL-2-amino-2-(2-bromo-5-hydroxyphenyl-acetyl | <0.1 |
| D-2-amino-2-(m-fluorophenyl)acetyl | <0.1 |
| D-2-amino-3-methylbutyryl | 0.2 |
| D-2-amino-3-phenylpropionyl | 0.39 |
| D-2-amino-2-(p-hydroxyphenyl)acetyl | <0.1 |
| 1-aminocyclohexylcarbonyl | 25 |

What is claimed is:
1. A complex of the formula

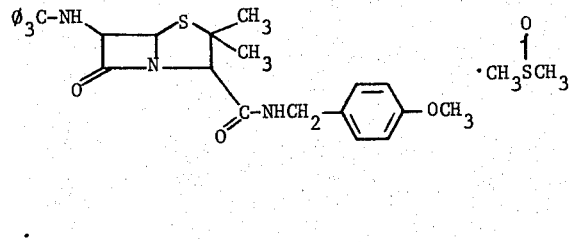

* * * * *